United States Patent
Sokol et al.

(10) Patent No.: US 6,254,703 B1
(45) Date of Patent: Jul. 3, 2001

(54) QUALITY CONTROL PLASMA MONITOR FOR LASER SHOCK PROCESSING

(75) Inventors: David W. Sokol, Dublin; Craig T. Walters, Powell; Harold M. Epstein, Columbus; Allan H. Clauer, Worthington; Jeffrey L. Dulaney, Dublin; Mark O'Loughlin, Galloway, all of OH (US)

(73) Assignee: LSP Technologies, Inc., Dublin, OH (US)

( * ) Notice: Subject to any disclaimer, the term of this patent is extended or adjusted under 35 U.S.C. 154(b) by 0 days.

(21) Appl. No.: 09/256,333

(22) Filed: Feb. 19, 1999

(51) Int. Cl.[7] .................................................. C21D 1/54
(52) U.S. Cl. ................................. 148/508; 266/99
(58) Field of Search .............................. 148/508; 266/99; 427/554; 374/32

(56) References Cited

U.S. PATENT DOCUMENTS

| | | | |
|---|---|---|---|
| 5,571,575 | * 11/1996 | Takayanagi | 427/554 |
| 5,741,559 | * 4/1998 | Dulaney | 427/554 |
| 5,980,101 | * 11/1999 | Unternahrer et al. | 374/32 |
| 5,987,042 | * 11/1999 | Staver et al. | 372/30 |
| 6,002,706 | * 12/1999 | Staver et al. | 372/108 |

OTHER PUBLICATIONS

Laser Generation of 100–kbar Shock Waves In Solids, by Craig T. Walters (3 pages) no date.

* cited by examiner

Primary Examiner—Scott Kastler
(74) Attorney, Agent, or Firm—Randall J. Knuth

(57) ABSTRACT

A method and apparatus for quality control of laser shock processing. The method includes measuring emissions and characteristics of a workpiece when subjected to a pulse of coherent energy from a laser. These empirically measured emissions and characteristics of the workpiece are correlated to theoretical shock pressure, residual stress profile, or fatigue life of the workpiece. The apparatus may include a radiometer or acoustic detection device for measuring these characteristics.

22 Claims, 1 Drawing Sheet

QUALITY CONTROL PLASMA MONITOR FOR LASER SHOCK PROCESSING

BACKGROUND OF THE INVENTION

1. Field of the Invention

The present invention relates to a system for monitoring a workpiece during laser shock processing, and in particular, a system for monitoring the pressure pulse applied to a workpiece during laser shock processing.

2. Description of the Related Art

Laser shock processing involves a pulse of coherent radiation to a piece of solid material (workpiece) to produce shockwaves therein. The produced shockwave cold works the solid material to impart compressive residual stresses within the solid material. These compressive residual stresses improve the fatigue properties of the solid material.

Current laser shock processing utilizes two overlays: a transparent overlay (usually water), and an opaque layer (usually an oil based paint or black plastic tape). During processing, a laser beam is directed to pass through the transparent overlay and is absorbed by the opaque layer, causing a rapid vaporization of the opaque layer (plasma creation) and generation of a high-amplitude shockwave. The shockwave cold works the surface of the part and creates deep compressive residual stresses which provide an increase in fatigue properties of the workpiece. A workpiece is typically processed by employing a matrix of overlapping spots that cover the fatigue-critical zone of the part.

Currently, there is no known real-time method for measuring the shock pressure applied to a workpiece during laser shock peening. While commercial pressure gauges, such as special quartz gauges or PVDF gauges are available to make pressure measurements, these gauges must be used offline (not in real time on a workpiece). Furthermore, these gauges are single-use devices.

A quartz gauge is based on the piezoelectric behavior of quartz crystals. When a pressure is applied to one surface of a quartz crystal, an electric current proportional to the stress difference between this surface and the opposite surface is produced between electrodes attached to these surfaces. The current then passes through a resistor and the voltage measured across the resistor is proportional to the difference in the stress between the opposite surfaces. In the "thick gauge" mode, most or all of the shockwave passes into the thickness of the gauge before it reaches the opposite surface of the crystal. This enables one to measure the entire shockwave profile directly.

One problem with current laser shock processing systems is that there is no real-time method or apparatus for measuring shock pressure or plasma characteristics during laser shock peening or correlating them to the imparted deep compressive residual stresses in a workpiece. Previous methods of measuring a pressure pulse applied to a workpiece included use of a quartz gauge. The disadvantage of using a quartz gauge is that a quartz gauge is a single use instrument. In addition, the use of a quartz gauge does not permit real-time measuring of a pressure pulse while processing a workpiece. The use of a quartz gauge is limited to measuring the pressure pulse applied to a workpiece either before or after laser shock processing (i.e., not real time).

Another problem in the art is that there is no method for correlating plasma characteristics to a pressure pulse applied to a workpiece.

Another problem in the art is that there is no known method or apparatus for real-time determination of imparted compressive residual stresses in a workpiece during laser shock peening. Currently, the method of evaluating an imparted residual stress profile is to measure the residual stresses using x-ray diffraction techniques. In order to use x-ray diffraction, a workpiece is normally removed from the laser shock processing station and placed in an x-ray machine, wherein an x-ray beam is directed to the workpiece surface to measure the residual stresses at that surface. In order to get an in-depth profile, a sequence of thin layers is removed from the surface by electropolishing, then the surface residual stresses are measured between each electropolishing step. If only the residual stress at the original surface of the workpiece is measured, the measurements also includes the unknown effects of previous surface finishing processes. These usually vary from part to part and could be differentiated from the stresses imparted by laser shock peening. The technique of x-ray diffraction for in-depth profiles is a destructive method for evaluating compressive residual stresses imparted in a workpiece by laser shock peening. The use of x-ray diffraction is limited to post-laser shock peening analysis. Therefore, x-ray diffraction cannot be used as a real time method for determining imparted compressive residual stresses.

SUMMARY OF THE INVENTION

The present invention is a method and apparatus for monitoring laser shock processing of a workpiece. The method and apparatus includes detecting spectral and acoustic energy emitted from a workpiece or the energy absorbing layer applied to the workpiece. The acoustic and spectral emissions may be correlated to the pressure pulse applied to a workpiece, the residual stress profile produced in the workpiece, and the fatigue life of the workpiece.

The invention, in one form thereof, is an apparatus for monitoring laser shock processing of a workpiece. The apparatus includes a material applicator for applying an energy absorbing material to the workpiece. A transparent overlay applicator applies a transparent overlay onto the workpiece over the energy absorbing layer. A laser is operatively associated with the energy absorbing layer and there is at least one radiometer. In one particular further embodiment, the energy absorbing layer may contain a dopant.

The invention, in another form thereof, is a method for real time monitoring laser shock processing of a workpiece. The method includes applying an opaque overlay to the workpiece. A beam of coherent energy is directed to the workpiece to vaporize a portion of the opaque overlay and to create a plasma which emits energy therefrom. A portion of the energy emitted from the plasma is monitored. In a further embodiment, spectral emissions are detected from the emitted energy. In an alternate embodiment, acoustic emissions are detected within the emitted energy.

The invention, in yet another form thereof, is a method for real time monitoring the laser shock peening of a workpiece. The method includes applying a transparent overlay to a workpiece and directing a beam of coherent energy to the workpiece through the transparent overlay and to create a plasma which emits energy therefrom. A portion of the energy emitted from the plasma is monitored. In a further embodiment, spectral emissions are detected from the plasma emitted energy. In an alternate embodiment, acoustic emissions are detected from the emitted energy. In alternate further embodiments, a feature of the spectral emissions or acoustic emissions are correlated to the shock pressure applied to the workpiece.

The invention, in another form thereof, is a method for real time monitoring the laser shock peening of a workpiece. The method includes applying an opaque overlay to a workpiece and directing a beam of coherent energy to a workpiece to vaporize a portion of the opaque overlay and create a plasma thereon. The temperature of the plasma is monitored. In a further embodiment, the plasma temperature is correlated to the residual stress profile left in the workpiece.

The invention, in yet another form thereof, is a method for real time monitoring the laser shock peening of a workpiece. The method includes applying a transparent overlay to a workpiece. A beam of coherent energy is directed to a workpiece through the transparent overlay and creates a plasma thereon. The temperature of the plasma is monitored. In further alternate embodiments, the plasma temperature is correlated to the shock pressure of the workpiece, the residual stress profile left in the workpiece, and the fatigue life of the workpiece.

One advantage of the present invention is the ability to correlate characteristics and emissions from a workpiece and overlay during laser shock peening to a shock pressure, compressive residual stress profile, or fatigue life of a workpiece. Characteristics or features, such as acoustic emissions and spectral emissions are correlated to a shock pressure, compressive residual stress, or fatigue life of a workpiece. As a result, monitoring such characteristics allows one to predict the shock pressure and compressive residual stresses or fatigue life of a workpiece in real time.

Another advantage of the present invention is a nondestructive technique to predict the compressive residual stresses imparted in a workpiece during laser shock processing. Through the correlation of acoustic and spectral emissions from a workpiece or overlay to a shock pressure and residual stress profiles imparted to the workpiece, one can determine the effectiveness or success of the laser processing of the workpiece. Therefore, it is no longer necessary to use a destructive technique, such as x-ray diffraction, to evaluate the imparted compressive residual stresses during laser shock processing.

Another advantage of the present invention is the ability to do real time quality control of a workpiece subjected to laser shock processing. Since measured characteristics of acoustic and spectral emissions may be correlated to shock pressure and compressive residual stresses imparted in a workpiece, one can perform quality control in real time of a laser shock processed workpiece. By measuring acoustic or spectral emissions, one can determine the imparted compressive residual stress of a workpiece. If the correlated compressive residual stress is not within a predetermined or desired range, additional laser shock processing may be done to ensure the desired compressive residual stress in the workpiece is achieved.

Prior to this invention, there was no known real time technique available for determining the compressive residual stresses imparted in a specific workpiece to provide quality control of that specific workpiece. Prior to this invention, a technique of random or regular testing was done on a workpiece subsequent to laser shock peening a lot of workpieces. The randomly selected workpiece was subjected to the destructive technique of x-ray diffraction in which the imparted compressive residual stress was measured in the randomly selected workpiece. The results of the randomly selected workpiece's residual stress profile was then extrapolated to non-tested workpieces processed under the same condition, to estimate the non-tested workpieces' imparted compressive residual stress profile.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
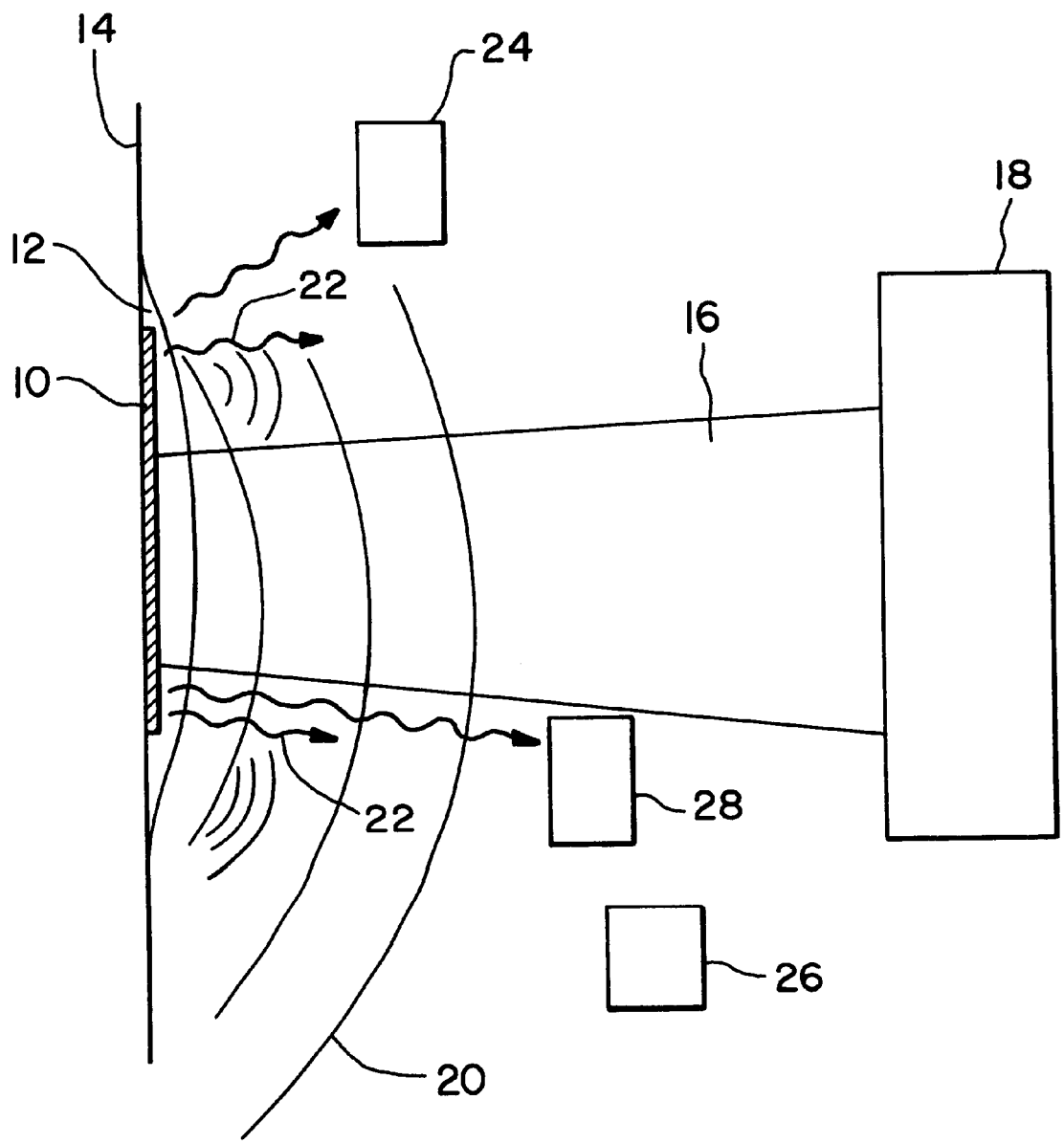
FIG. 1 is a cross sectional, diagrammatic view of an apparatus for monitoring laser shock processing of a workpiece according to the present invention.

The improvements in fatigue life produced by laser shock processing are the result of residual compressive stresses developed in the irradiated surface retarding fatigue crack initiations and/or slowing the crack propagation rate. A crack front is the leading edge of a crack as it propagates through the solid material. Changes in the shape of a crack front and slowing of the crack growth rate when the crack front encounters the laser shocked zone in a laser shock processing condition have been shown. Laser shock processing is an effective method of increasing fatigue life in metal workpieces by treating fatigue critical regions.

For a more thorough background in the prior history of laser shock processing and that of high power processing of engineered materials, reference can be made to U.S. Pat. No. 5,131,957. Such patent is hereby incorporated by reference. This patent also shows a type of laser and laser configuration adaptable for use with the present invention. Another type of laser adaptable for use with the present invention is that of a Nd-Glass laser manufactured by LSP Technologies, Inc. of Dublin, Ohio.

Overlays are applied to the surface of the target workpiece being laser shock processed. These overlay materials may be of two types, one transparent to laser radiation and the other opaque to laser radiation. They may be used alone or in combination with each other, but it is preferred that they be used in combination with an opaque layer adjacent to the workpiece and the outer transparent layer being adjacent to the opaque layer.

Referring now to FIG. 1, components of one embodiment of an apparatus for monitoring laser shock processing of a workpiece are shown. Opaque overlay 10 and transparent overlay 12 are applied to workpiece 14. A beam of coherent energy or laser pulse 16 is directed from laser 18 through transparent overlay 12 and is absorbed by opaque overlay 10.

During laser shock processing, the laser pulse 16 is absorbed by opaque layer 10, which is quickly vaporized, producing a plasma. The plasma is confined by the transparent overlay 12 resulting in a pressure pulse applied to workpiece 14. The pressure pulse creates a shock wave within workpiece 14, which imparts deep compressive stresses within workpiece 14.

When opaque layer 10 is hit with a laser pulse 16, acoustic energy 20 and spectral emission 22 are emitted from workpiece 14 and opaque overlay 10. Radiometer 24 detects spectral emissions and acoustic detector 26 detects acoustic energy emissions.

Radiometer 24 measures a portion of the optical spectrum and is directed toward workpiece 14, and in particular, that of opaque overlay 10 such that radiometer 24 may measure the temperature of the workpiece and/or the plasma when they are irradiated by a laser pulse 16.

In addition to radiometer 24, the temperature of workpiece 14 may be measured by other means. For example, a thermocouple or simple IR thermometer (not shown) may be used to measure the rear surface temperature of the workpiece separately. Traditionally, an IR thermometer is a type of radiometer normally used to measure much lower temperatures than that of the plasma.

During laser shock processing, spectral emissions 27 are emitted from various components involved in laser shock processing. The spectral emissions 22 are the result of workpiece 14 and/or opaque layer 10 being subjected to a laser pulse 16. When workpiece 14 is vaporized to produce a plasma, spectral emissions 22 are emitted. In addition, when transparent overlay 12, in contact with opaque overlay 10 or workpiece 14 is vaporized to produce a plasma, spectral emissions 22 are emitted.

Opaque overlay 10 may include a dopant. The dopant material may result in a detectable optical or spectral emission. The opaque or energy absorbing layer 10 may also fluoresce when the opaque layer 10 is subjected to pressure or temperature.

Alternatively or in addition to a dopant in opaque overlay, transparent overlay 12 may include a dopant. The dopant material may result in a detectable optical or spectral emission. The opaque or energy absorbing layer 10 may also fluoresce when the opaque layer 10 is subjected to pressure or temperature.

The dopant may be dispersed in particle form, solute form, or any recognized dispersant form in the opaque overlay to a transparent overlay 12. The dopant may also consist of micro-spheres filled with a marker. When the micro-spheres are subjected to temperature or pressure, the micro-spheres are crushed or fractured, releasing their marker. The released marker is then detected by radiometer 24 or other detection devices.

During operation of the present invention, when a beam of coherent energy or laser pulse 16 is absorbed by opaque layer 10, acoustic energy 20 is emitted from workpiece 14, resulting from the effects of the shockwave and from the rapidly expanding plasma. Although not depicted in FIG. 1, a plurality of radiometers may be utilized. For example, multiple radiometers, each one observing a different band such as UV, visible, and IR, or narrower bands may be utilized.

For real-time or in-process monitoring of the effectiveness of laser shock processing of workpieces, means and methods for measuring the characterizing parameters of temperature and pressure in the plasma formed in front of the material by the laser pulse are needed. This plasma is the source of the shockwave, which produces a beneficial modification of the material as it traverses the workpiece. These parameters (temperature and pressure) are not independent of one another but are related by a complex equation of state. The parameters follow temporal histories depending upon this equation of state, the transparent overlay material composition and thickness, the opaque overlay material composition and thickness, the substrate compliance, the laser beam irradiance and temporal history, and the laser wavelength.

It is not necessary to have a complete predictive model for the plasma in order to use these parameters to monitor the laser shock processing conditions. By performing measurements of plasma temperature and pressure (both magnitude and temporal history, i.e., signatures) under laser and material conditions for which known processing results are obtained, temperature and pressure sensors can be calibrated to these processing results for use as real time or in- process quality control monitors. The temperature of the plasma may be able to provide an indirect measure of the plasma pressure, which is directly related to the shock intensity in the material (and hence, laser shock processing effectiveness). Temperature measurements can also detect the absence of the transparent overlay, the absence of the opaque overlay, or both.

An indirect pressure measurement may be utilized in the present invention. A simple model for the evolution of the plasma formed in laser shock processing is the piston model. In this model, a fixed amount of the opaque overlay is heated adiabatically by absorption of the laser pulse. The model predicts a power law dependence of peak pressure Po on peak irradiance, G, $Po=G^{1/2}$, for fixed irradiance temporal profile, and a fixed fraction of incident energy given to ionization. Although the model oversimplifies the physics, the basic dependence of pressure on irradiance has been verified experimentally. Under these same assumptions, the temperature should follow the same power law dependence on irradiance. Temperature in the confined plasma (confined by transparent overlay) has been measured to be about 8,000 K at 1 $GW/cm^2$, but the irradiance dependence has not been confirmed. For normal laser shock processing conditions, the temperature should be in the range of 15,000 K (at 3.5 $GW/cm^2$) to 25,000 K (at 10 $GW/cm^2$) and pressure should be close to a linear relationship with a measured temperature.

The measurement of plasma temperature is relatively uncomplicated for plasmas that emit radiation as a blackbody in portions of the spectrum. If a radiometer is arranged to view the plasma with filters admitting plasma light in a narrow spectral range where the plasma is radiating as a blackbody, then the radiometer output signal can be directly related to plasma temperature by the Planck function. Such a radiometer can be constructed with simple lenses, optical filters, and a silicon PIN photodiode for the UV/VIS/NIR portions of the spectrum.

Alternate means of measuring the plasma temperature rely on viewing the plasma in portions of the spectrum where individual spectral lines of atomic or ionic species in the plasma are visible. The atomic or ionic species might be the abundant species of the overlay materials, such as C,H,O or might be trace elements introduced as dopants for the purpose of monitoring temperature. Trace elements should normally be benign low atomic number elements such as B, Li, N, Na, Mg, Al, Si, but could be any element with co-located strong lines arising from different energy levels. Because pumping rates of the upper levels are strongly temperature dependent, ratios of line emissions provide a sensitive means of measuring plasma temperature. The line ratio approach may be particularly useful for laser shock processing because the plasma temperature is a weak function of irradiance and a sensitive measurement of temperature is desirable. Implementation of the line ratio measurement can be achieved with three fast photodiodes and three narrow-band filters, two centered on the target emission lines and one on the continuum in between.

The present invention can be utilized to detect the absence of an overlay. In the case where the transparent overlay is missing, the plasma is unconfined and quickly expands to low density. The effect of the expansion is to put more energy into fewer atoms than in the confined plasma case.

This leads to higher plasma temperatures. Prior research has shown that the temperature dependence on fluence for expansion into a vacuum follows a power law, $F^{1/2}$, where F is incident beam fluence. Typical temperatures for a black paint overlay with no confinement are 50,000 K at 200/J/cm$^2$ (8 Gw/ cm$^2$) and 110,000 K at 1000/J/cm$^2$ (40 Gw/cm$^2$) for a 25-ns pulse. These temperature levels are greater than those predicted for the confined case at similar fluences. Temperatures will be even higher if there is time to establish a laser-supported detonation wave in the air in front of the expanding plasma, which is the condition expected for a missing transparent overlay. A thin overlay might also be detected by an increase in plasma temperature in the middle of the laser pulse when the reflected shock wave from the water-free surface arrives at the water-plasma surface. Plasma temperature measurements may by implemented by the methods mentioned above.

An alternative method for determining the absence of the transparent overlay, is to dope the overlay with a small amount of fluorescent material. Under normal operation, the intense UV from the plasma will cause the overlay to fluoresce at characteristic wavelengths. The fluorescent emissions would be missing or weak for a missing or thin overlay. The fluorescent materials or viewing geometries must be selected such that the emissions dominate the background plasma radiation. This might be accomplished with dyes or dopant materials having fluorescent lifetimes long compared to the plasma lifetime. In such cases, fluorescing droplets of overlay material could be detected after they are ejected from the surface and are distant from the background plasma.

A third alternative method for determining the absence of a transparent overlay is to sense the overlay droplet cloud by shadowgraphy or light scattering under normal operations. The cloud signatures would be missing or altered if the overlay were missing or thin.

The present invention may also be used to detect the absence of the opaque overlay. In the event that the opaque overlay is missing, the temperature signature would be different than normal, because, in general, the equation of state of the substrate material will be quite different from that of the opaque overlay (e.g., iron versus carbon). A more sensitive detector, however, will be a fast photodiode with a line filter centered on a known strong emission line of a major constituent of the substrate. Generally, substrate species can be found that typically are not present in either the transparent overlay or the opaque overlay.

The strength of a shockwave imparted to the workpiece is ideally determined by a direct measurement of pressure in the plasma. An indirect measurement of pressure may be done using plasma emissions and spectroscopic techniques. Stark broadening of spectral lines occurs with increasing electron density due to the associated increase in average local electric field. This mechanism has been used to measure electron density in plasmas containing oxygen. The peak of the oxygen emission line also exhibits a red shift with increasing electron density. The electron density multiplied by temperature contributes to the total plasma pressure in a predictable manner. Thus, spectral line broadening and/or shifts in selected elemental emission lines, combined with temperature measurements, should provide a measure of the plasma pressure. These measurements may be implemented with a spectrometer or an array of fast photodiodes with narrow-band line filters selected to encompass the line of interest. The atomic specie used to serve as a pressure indicator may be any specie naturally occurring in the opaque or transparent overlay material such as C, H, or O, or it may be added to the overlay materials as a trace element specifically for the purpose indicating pressure, e.g., B, Li, N, Na, Mg, Al, or Si.

The spectroscopic measurements of pressure discussed previously require careful emission measurements of the plasma radiation in spectral regions where the radiation is not dominated by the continuum. The benefit of this approach is the advantage of real time in-process monitoring of the plasma pressures generated.

Once the temperature and/or pressure history in the plasma have been measured, the measured record may be correlated to the deep compressive residual stresses imparted in the workpiece. The correlation involves laser shock processing a workpiece to impart compressive residual stresses while measuring temperature and/or pressure histories of the plasma created. A residual stress profile of the workpiece is then measured using the x-ray diffraction technique. A correlation or look-up table is created which maps plasma pressure and temperature histories to the x-ray diffraction-measured residual stress profile. Once this correlation table has been created, one can look up the predicted residual stress profile from the empirical data of temperature and pressure temporal histories.

A residual stress profile may be determined by using x-ray diffraction techniques commonly known in the art. For example, an x-ray beam may be directed to a metal surface where the measurement is desired and the x-ray beam is diffracted from the surface at an angle related to the spacing of the atomic planes diffracting the beams. If the spacing between these planes changes, the angle of the diffraction peak shifts slightly. The inter-planar distance will increase or decrease if the local elastic strains in the lattice are tensile or compressive, respectively. By measuring the shift in the diffraction peak, the elastic strain in the lattice can be determined and through the elastic modulus, the residual stress causing this strain can be calculated. To get the in-depth profile, a thin layer of the surface is removed by electropolishing (grinding will create its own residual stresses in a thin surface layer), and the measurement is repeated in the same location. This step-wise sequence is continued to the total depth of measurement desired. A modeling program is then used to apply corrections to the measured values to account for the stress relaxation caused by removing the successive layers of material.

The measured temperature and pressure history may also be correlated to fatigue life in a similar manner in which empirically measured temperature and pressure is correlated to a measured residual stress profile. Fatigue life may be measured by placing a workpiece in a machine that is exposed to a cyclic strain or stress. It is usually defined in terms of the number of cycles to failure under the testing conditions used. Fatigue life is defined as the maximum number of cycles to failure at a given cyclic stress amplitude.

The method of correlating empirical temperature and pressure to fatigue life consists of laser shock processing while recording temperature and pressure of the produced plasma. Fatigue life of the laser shock processed workpiece is then measured. Next, the measured fatigue life is correlated to the measured temperature and pressure. These steps are repeated for varying combinations of measured temperatures and pressures to create a chart, graph, or correlation table which correlates fatigue life to the measured temperatures and pressures. With this table, one can use empirically measured temperature and pressure to determine a predicted fatigue life in a workpiece.

The measured acoustic signal or energy emitted during laser shock processing may also be used for determining a residual stress profile, fatigue life, or shock pressure applied to a workpiece. The method includes recording empirical data of acoustic signatures or acoustic energy emitted during different laser shock processing conditions. Subsequent to laser shock processing, a residual stress profile and fatigue life is determined, as described above. A correlation table, chart, or graph is then created which relates empirically recorded acoustic energy to workpiece characteristics, such as residual stress profile or fatigue life. This correlation table, chart, or graph may then be used in subsequent laser shock processing cycles for determining a predicted residual stress profile, fatigue life, or shock pressure applied to a workpiece through empirically recorded emitted acoustic energy.

Quality control is achieved through use of the present invention. One is now able to determine a predicted residual stress profile or fatigue life of a workpiece from the observed laser processing conditions in real time. This allows one to determine the consistency of laser shock processing conditions during production processing. If the predicted residual stress profile, fatigue life, or pressure pulse is not within a predetermined or desired range, one can now reprocess the workpiece, as necessary. In addition, one can use this method for producing uniform compressive residual stresses in a workpiece.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An apparatus for monitoring laser shock processing of a workpiece, comprising:
   a material applicator for applying an energy absorbing material onto the workpiece;
   a transparent overlay applicator for applying a transparent overlay onto the workpiece over said energy absorbing layer;
   a laser operatively associated with said energy absorbing layer to laser shock process the workpiece; and
   at least one radiometer measuring energy from the laser shock processed workpiece.

2. The apparatus of claim 1 further comprising a second radiometer, said radiometers detecting energy at different wavelengths.

3. The apparatus of claim 1 wherein said energy absorbing material contains a dopant.

4. The apparatus of claim 3 wherein the presence of said dopant results in a detectable optical signal when said dopant is subjected to pressure.

5. The apparatus of claim 3 wherein the presence of said dopant results in a detectable optical signal when said dopant is heated.

6. The apparatus of claim 1 wherein said energy absorbing material fluoresces when said energy absorbing material is subjected to heat.

7. The apparatus of claim 1 wherein said energy absorbing material fluoresces when said energy absorbing material is subjected to pressure.

8. The apparatus of claim 1 wherein said energy absorbing material emits optical energy detectable by said radiometer.

9. The apparatus of claim 3 wherein said dopant consists of micro-spheres filled with a marker.

10. A method for real-time monitoring the laser shock peening of a workpiece comprising the steps of:
    applying an opaque overlay to a workpiece;
    directing a beam of coherent energy to a workpiece to vaporize a portion of said opaque overlay and create a plasma thereon; and
    monitoring the temperature of said plasma.

11. The method of claim 10 further comprises the step of creating a shock pressure on the workpiece: and
    determining the shock pressure on the workpiece, using the plasma temperature.

12. The method of claim 10, further comprising the steps of creating a residual stress profile in the workpiece; and
    determining the residual stress profile provided in the workpiece, using the plasma temperature.

13. The method of claim 10, wherein said step of monitoring the plasma temperature further comprises the step of:
    determining the fatigue life of the workpiece, using the plasma temperature.

14. A method for real-time monitoring the laser shock processing of a workpiece comprising the steps of;
    applying a transparent overlay to a workpiece;
    directing a beam of coherent energy to a workpiece through said transparent overlay and create a plasma thereon; and
    monitoring the temperature of said plasma.

15. The method of claim 14, wherein said step of monitoring the plasma temperature further comprises the step of:
    determining the shock pressure on the workpiece, using the plasma temperature.

16. The method of claim 14, wherein said step of monitoring the plasma temperature further comprises the step of:
    determining the residual stress profile provided in the workpiece, using the plasma temperature.

17. The method of claim 14, wherein said step of monitoring the plasma temperature further comprises the step of:
    determining the fatigue life of the workpiece, using the plasma temperature.

18. The apparatus of claim 6, further comprising:
    a laser pulse of coherent energy; and
    said laser pulse produces said heat.

19. A method for real-time monitoring the laser shock peening of a workpiece comprising the steps of:
    applying a transparent overlay to the workpiece;
    directing a beam of coherent energy to a workpiece through said transparent overlay and creating a plasma which emits energy therefrom; and
    monitoring a portion of the energy emitted from said plasma, the monitoring operation for providing a measure of at least one characteristic of the plasma energy emission, said monitoring step including detecting spectral emissions from said plasma emitted energy and determining the presence of a transparent overlay on the workpiece using a feature of said spectral emissions.

20. A method for real-time monitoring the laser shock peening of a workpiece comprising the steps of:
    applying a transparent overlay to the workpiece;
    directing a beam of coherent energy to a workpiece through said transparent overlay and creating a plasma which emits energy therefrom; and monitoring a portion of the energy emitted from said plasma, the monitoring operation for providing a measure of at least one characteristic of the plasma energy emission, said monitoring step including detecting acoustic emissions from said plasma emitted energy and determining the presence of a transparent overlay on the workpiece using a feature of said acoustic emissions.

21. A method for real-time monitoring the laser shock peening of a workpiece comprising the steps of:

applying a transparent overlay to the workpiece;

directing a beam of coherent energy to a workpiece through said transparent overlay and creating a plasma which emits energy therefrom; and monitoring a portion of the energy emitted from said plasma, the monitoring operation for providing a measure of at least one characteristic of the plasma energy emission, said monitoring step including detecting spectral emissions from said plasma emitted energy and determining the presence of an opaque overlay on the workpiece using a feature of said spectral emissions.

22. A method for real-time monitoring the laser shock peening of a workpiece comprising the steps of:

applying a transparent overlay to the workpiece;

directing a beam of coherent energy to a workpiece through said transparent overlay and creating a plasma which emits energy therefrom; and monitoring a portion of the energy emitted from said plasma, the monitoring operation for providing a measure of at least one characteristic of the plasma energy emission, said monitoring step including detecting acoustic emissions from said plasma emitted energy and determining the presence of an opaque overlay on the workpiece using a feature of said acoustic emissions.

* * * * *